US000001093H

United States Statutory Invention Registration [19]

[11] Reg. Number: H1093

Huston

[43] Published: Aug. 4, 1992

[54] HCL MONITORING APPARATUS AND METHOD FOR PROCESS GAS STREAMS

[75] Inventor: Gregg C. Huston, LaBelle, Pa.

[73] Assignee: The United States of America as represented by the United States Department of Energy, Washington, D.C.

[21] Appl. No.: 461,963

[22] Filed: Jan. 8, 1990

[51] Int. Cl.[5] ..... G01N 33/00; G01N 21/00; G01N 30/96

[52] U.S. Cl. ..... 436/101; 436/121; 436/122; 436/123; 422/62; 422/90; 422/88

[58] Field of Search ..... 436/100, 121, 122, 123 (U.S. only); 422/62, 90, 88 only); 422/62, 90, 88

[56] References Cited

PUBLICATIONS

Wachter, J. K., "Development of an extractive, continuous monitor to analyze hydrogen chloride in coal derived process streams." Energy Res. Abstr. 1988 13(23) 28 pages 1988.

Afendik, K. F. et al. "Continuous method for the determination of hydrochloric acid in waste gases . . . " Deposited Doc., SPSTL 303 khp-D80, 9 pages.

Wachter, J. et al. "Hydrogen chloride monitor", Morgantown Energy Technol. Cat., Direct Util. Contract Meet., 1985 423-30.

Cram, J. M. et al. "The Essene of Organic Chemistry", Addison-Wesley Pub Co., Philippines 1978 pp. 113-114.

Gregg G. Huston, et al., "Development of an Extractive Continuous Monitor for Hydrogen Chloride Analysis of Coal-Derived Process Stream," Analytical Letters, 22(1), 269-292 (1989).

*Primary Examiner*—Robert L. Stoll
*Assistant Examiner*—C. Harris
*Attorney, Agent, or Firm*—David E. Breeden; Stephen D. Hamel; William R. Moser

[57] ABSTRACT

An HCl monitor is provided for the extractive analysis of high-temperature, high-pressure, coal-derived process streams. The monitor is capable of HCl concentration measurement in the presence of all known coal gasification products, with detection being based on the ability of HCl to protonate a high boiling alcohol (solvent) and, thus, enhance the conductivity of the alcohol. Conductivity is then related to HCl concentration. The observed high degree of sensitivity that can be achieved is a result of analyte preconcentration prior to the conductivity measurement due to the fast dissolution rate of HCl into the alcohol solvent, coupled with a large analyte gas-to-solvent ratio.

4 Claims, 4 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

HCL MONITORING APPARATUS AND METHOD FOR PROCESS GAS STREAMS

FIELD OF THE INVENTION

The present invention relates to a method and apparatus for monitoring the HCL content of gasification process streams.

BACKGROUND OF THE INVENTION

One new approach in promoting the use of coal for other than conventional energy production is the potential coupling of a coal gasifier with a molten carbonate fuel cell (MCFC) power plant. However, some contaminants, such as HCl, that may be present in the input gasification process stream are known to degrade MCFC performance. Extensive and accurate characterization of coal gasification streams with respect to such trace contaminants is oftentimes lacking, primarily due to the inadequacies of conventional sampling and analytical methods. Thus, a need exists for an effective on-line HCl monitoring system for use in the continuous and extractive analysis of high-pressure, high-temperature, coal-derived process streams, and in particular, for the coal gasification process input stream to a MCFC.

There are a number of different types of fuel cells currently being developed. However, the MCFC appears to be well suited for use with coal gasifiers, due to the compatibility of the operating temperatures and product gas composition. For example, an oxygen-blown pressurized fluidized-bed gasifier system may be an attractive choice for coupling with a MCFC because of the high CO and $H_2$ concentrations and very low volatile hydrocarbon concentrations generated by this gasifier. Recent advances in hot gas cleanup technologies have brought the possibility of coupling the coal gasification process with a MCFC closer to a practical realization.

There are several reasons for developing a HCl monitoring system. The quantities of HCl that exit a coal-fired gasifier have not been directly measured. However, theoretical calculations indicate that the concentrations may exceed the tolerance levels of a MCFC. Hot gas cleanup technology, as applied to HCl removal, is at a relatively early stage in development and the effectiveness thereof is unknown due in part to the absence of a suitale HCl analysis system. An HCl monitoring system would be necessary to monitor the process effluent to assess any excursions over damage thresholds and, thus, to prevent MCFC damage due to cleanup system failure. The ideal requirements of such a system are continuous monitoring, real-time output, HCl specificity, a broad linear range, and reasonable accuracy and precision.

The amount of HCl that is expected to be present in coal gasification streams has been calculated. Based on thermodynamic calculations and the average ranges of chloride in coals ion the United States and residual chloride in gasifier ash, it has been calculated that the expected range of HCl concentrations in gasifier process (raw) streams to be between 1 to 500 ppmv. (See, e.g., Cicero, et al, *Advanced Development of a Pressurized Ash Agglomerating Fluidized-Bed Coal Gasification System*, p. 249, DOE/MC/19122-1810, NTIS/-DE85010517 (1983); and *Monitoring Contaminants in Coal-Derived Gas for Molten Carbonate Fuel Cells*, TRW, Energy Engineering Division, DOE/METC-82-44 (1981).

Some experimental work has been performed to determine the effects of HCl on MCFC operations. In a General Electric Final Report, *Development of Molten Carbonate Fuel Cells for Power Generation*, p. 554, DO-E/ET11319-T2, NTIS/DE81027028 (1980), the effects of 10 and 100 ppmv HCl on MCFC performance were assessed and it was concluded that the presence of HCl in the fuel gas at concentrations less than or equal to 10 ppm would not affect electrical output. On the other hand, concentrations greater than 10 ppm up to 100 ppm HCl may reduce electrical output. The effects of HCl on the cathode of the MCFC were also studied and severe degradation of MCFC performance was observed. In general, this work indicted that the corrosivity of HCl was the principal contributor to reduced MCFC performance. The effects of HCl on MCFC performance are also described in *Development of Molten Carbonate Fuel Cell Power Plant Technology*, United Technologies Corporation, DOE/ET15440-7, NTIS/-DE82009557D (1981). The limited research results reported indicate that HCl in the fuel gas had a deleterious effect on MCFC performance. A large loss of electrolyte (due to reactions of HCl with molten carbonate to form a product having high vapor pressure) may have accounted for all the effects observed.

Thermodynamic calculations described in Magee, et al, *The Effects of Halides on the Performance of Coal Gas Fueled Molten Carbonate Fuel Cells*, DOE/MC/23136-2236, NTIS/DE87001079 (1986), show that HCl should react quantitatively with molten carbonate (potassium or lithium) to form water, $CO_2$, and MCl (where M=K or Li). The vapor pressure of MCl was significant at MCFC operating conditions and thermodynamic calculations supported the observed electrolyte loss reported in the United Technologies reference.

In developing an analytical method for HCl analysis, a number of problems must be addressed. The matrix (of a gasifier process stream) is relatively complex, containing both organic and inorganic gaseous species. Some of the known and suspected chemical species that may be present in a gasifier stream include: CO, mid percentage; $CO_2$, low percentage; $H_2$, mid percentage; $CH_4$, low percentage; $N_2$, low percentage; $H_2O$; low/mid percentage; $H_2S$, high ppm; HCN, low ppm; COS, low ppm; $NH_3$, mid/high ppm; $SO_2$, high ppb to low ppm; HCl, low/mid ppm; Phenol, low ppm; Cl-salts, low ppm; $>C_2$-organics, mid ppm; and HF, low/mid ppm.

There are a number of qualitative and quantitative analytical methods used for detection of gas phase HCl. Gas chromatographic and spectroscopic techniques have been developed to various degrees of practical and applicable success. A brief discussion of these methods is provided hereinafter to illustrate the shortcomings thereof for use in the analysis of coal gasification process streams and to highlight the specific analytical problems to be addressed when analyzing HCl.

Gas chromatographic HCl methods are described, for example, in Baiker et al, "Analysis of CO, $CO_2$, $COCL_2$, HCl, and $Cl_2$ Gas Mixtures," *J. Chromatogr*, 147, pp. 453-355 (1978); Agliulov, et al, "Use of Gas Chromatography for the Analysis of Inorganic Compounds," *Tr. Khim. Khim. Tekhnol*, pp. 66-68 (1973); Zueva, et al, "Gas-Chromatographic Analysis of Tin and Antimony Chlorides," *Zh. Anal. Khim*, 31(1), pp. 185-187 (1976); Araki, et al, "Gas Chromatography of Reactive Inorganic Gases and Vapors," *Bunseki*

*Kagaku*, 12(3). pp. 450–457 (1963); and Runge, "Gas-Chromatographic Analysis of Inorganic Gases," *Z. Anal. Chem.*, 189, pp. 111–124 (1962). However, the methods disclosed are restricted to the analysis of high HCl concentrations, and preconditioning of the columns by multiple injections of HCl is required. Teflon was assumed to be the most inert substance with respect to HCl reactivity and was used for all gas wettable surfaces to the extent possible.

Because of the absorption problems associated with chromatographing HCl directly, indirect methods were developed involving the addition of a reagent to the sample to form products in stoichiometric proportion to HCl that were less reactive and more easily chromatographed. These methods are described in Baechmann, et al, "Gas-Chromatographic Determination of Small Traces of Hydrogen Chloride: Reaction with Epibromohydrin," *Mikfochia. Acta.*, (1(1-2), pp. 17-28 (1979); Vierkorn, "Determination of Trace Amounts of Hydrogen Chloride by Derivatization with Epoxides and Gas Chromatographic Separation," *J. Chromatogr.*, 186, pp. 219-226 (1979), and Petruj, J., "Determination of Hydrochloric Acid in Organic Solutions by Gas Chromatography," *Chromatographia*, 13(4), pp. 207-208 (1980). Such techniques, were only partially successful because of errors introduced by increased sample handling and loss of HCl due to adsorption to surfaces prior to the reaction.

The success of gas chromatography (GC) has been limited because HCl displays a strong tendency to migrate into and through macromolecular and polymeric structure of column packings. Thus, in addition to partitioning between the stationary liquid phase of the chromatographic column and the carrier gas, HCl also becomes partitioned between the stationary liquid phase and the solid support. Partitioning between interfaces other than the stationary liquid phase and carrier gas leads to irreproducible quantification (i.e., peak height of area) which is more pronounced at low solute concentrations. This problem is typical of most polar molecules. The polar molecule phenomena is described in many studies, although these studies do not specifically concern HCl. Normally, nonchromatographic partitioning is minimized by selection of a stationary liquid phase of sufficient polarity so as to decrease the rate of mass transfer of the solute in the liquid phase and prevent solute migration to the solid support. However, this approach is not viable for HCl since very polar stationary liquid phases contain hydroxyl, cyano, and other groups that react or strongly associate with HCl.

It has been found in work using gas chromatography for HCl analysis done by the inventor and those working with him that selection of tubing material, solid support, and stationary liquid phase is an unfavorable compromise. For many packed column methods glass tubing is used because it can be easily deactivated by bonding bulky organic constituents to surface silanol groups. The bulky groups sterically hinder the approach of polar molecules toward remaining adsorption sites (siloxane bridges, Lewis acid sites, remaining silanol groups, etc.) residing beneath the organic canopy. This type of deactivation is successful for larger polar molecules such as alcohols, ketones, and organic acids, but the small size of the HCl molecule facilitates penetration of the canopy which promotes it nonchromatographic adsorption. Although well-conditioned Teflon has been determined to be the best choice for tubing material and solid support for HCl analysis due to its low surface activity, only a stationary liquid phase that has less surface energy than Teflon could efficiently wet a Teflon solid support. Stationary liquid phases that approach this requirement are halocarbon oils/waxes. From preparatory work using halocarbon liquid phases with Teflon as the solid support it has been found that HCl still penetrates the structure of Teflon. Further, although the lighter halocarbon fractions coated Teflon more efficiently that heavier fractions, HCl migrated more freely through the lighter fractions which enhanced HCl interaction with the solid support. A compromise between coating efficiency and ease of HCl penetration to the solid support was found in the halocarbon fraction K352 (SUPELCO). Unfortunately when using the K352 liquid phase, reproducibility remained strongly dependent on the sample size, the time between determinations and the total number of prior determinations.

Spectroscopic studies of HCl have been ongoing for about 50 years although most work has not been pursued with the immediate goal of producing a routine analytical method. Some of the more recent analytical studies involve single and multiphoton IR laser absorption spectroscopy as described in Hartmann, H. J. et al, Coherent IR Spectroscopy of Gases Using Picosecond Pulses, *Infrared Phys.*, Vol. 25, No. 1/2, pp. 223-226 (1985).; Michaelis, W., et al, Sensitive Remote and In Situ Detection of Air Pollutants by Laser Light Absorption Measurements, *Presenius Z. Anal. Chem.* 317(3-4), pp. 286-292 (1984); Marché, P., et al, Ground-Based Spectroscopic Measurements of HCl. *Geophysical Research Letters*, Vol. 7, No. 11, pp. 369-872 (1980)); and multiphoton ionization spectroscopy as described in Spiglanin, G. A., et al, "Mass-Resolved Laser Ionization Spectroscopy of HCl," *Chemical Physics Letters*, Vol. 137, No. 5, pp. 414-420 (1987); Callaghan, R. et al, "Resonantly Enhanced Two-Photon Spectroscopy of HCl and DCl in the 77,000-87,000 $cm^{-1}$ Region," *J. Chem. Phys.* 86(110), pp. 5273-5280, (1987); Brown, M. A. et al, "Multiphoton Laser Spectroscopy of the Ion Pair and Rydberg States of HCl," Inst. Phys. Conf. Ser. No. 84: Section 9 Paper Presented at RIS 86, Swansea, Wales, pp. 317-318 (1986); Arepalli, et al, "Detection of Cl Atoms and HCl Molecules by Resonantly Enhanced Multiphoton Ionization," *Chemical Physics Letters*, Vol. 118, No. 1, pp. 88-92 (1985). Non-laser IR absorption has been used to quantify HCl in the flue gas as described in Berkhahn, W. et al, "IR Spectroscopic Measurement of HCl in Flue Gas Using the 677 IR HCl-Measuring System," *VGB Kraftwerkstechnik*, 63. No. 9, pp. 801-806 (1983), but this method is not applicable to gasifier streams owing to significant overlap of HCl and methane IR spectra. In fact this overlap is so severe that even very narrow band light sources (i.e., lasers) do not provide an immediate solution.

Another problem that surfaces when attempts are made to use IR spectroscopic methods for HCl analysis in sample streams containing methane is the difficulty in providing calibration. For laser-based methods a calibration technique that uses a reference band is most often employed. The reference band must be equally susceptible to optical perturbations caused by scattering by particles and weak IR-absorbing sample matrix components. Thus, the reference band is typically very close in wavelength range to the signal band. In addition to the problem of finding an analytical IR absorption band not overlapping with methane, a reference band must also be found that does absorb HCl and does not overlap with methane (or the reference band must be absorbed by methane to the same extent as the signal band). Further complicating matters would be temperature and pressure broadening and shift effects as described in Rao, D. R., et al, "Dicke Narrowing and Pressure Broadening in the Infrared Fundamental Band of HCl Perturbed by Ar," *Journal of Molecular Spectroscopy*. 122, pp. 16-27 (1987); Pine, A. S. et al, "$N_2$ and Air Broadening in the Fundamental Bands of HCl and HF," *Journal of Molecular Spectroscopy*. 122, pp. 41-55. (1987); Looney, J. P., et al, "Air Broadening of the Hydrogen Halides—I. $N_2$-Broadening and Shifting in the HCl Fundamental," *J. Quant. Spectrosc. Radiat. Transfer*. Vol. 37, No. 6, pp. 547-557 (1987); which would probably necessitate an extractive sample processing method such as a supersonic jet spectroscopy.

Recently, promising ultra violet spectroscopic methods have been described in the references referred to above. However, these were all multiphoton ionization methods and were primarily concerned with assigning transitions to be the observed spectra; moreover, more basic research will be required before this method can be applied to analysis of trace species in complex sample matrices.

Photoacoustic detection of HCl is described in Fried, A. Photoacoustic Detection of HCl. *Optics Letters*. Vol. 8, No. 3, pp. 160-162, (1983). This method is IR based and, therefore, has the same limitations as other IR spectroscopic methods.

SUMMARY OF THE INVENTION

In accordance with the invention, an improved method and apparatus are provided for monitoring the HCl content of gasification process streams. Several characteristics of HCl have been relied on in the development of the invention. More specifically, it has been noted that HCl is by far the strongest Bronsted acid constituent of gasification process streams and that HCl greatly increases the conductivity of alcoholic solvents (see Tourky, A. R., et al., "A Contribution to the Abnormal Mobility of Hydrogen Ion (Parts 1 and 2)," *Egypt. J. Chem.*, 1, No. 1, pp. 1-21 (1958); Tourky, A. R., et al., "A Contribution to the Abnormal Mobility of the Hydrogen Ion (Part 3), and "*Egypt J. Chem.*, 1, No. 2, pp. 187-204. (1958)). In addition, HCl has a relatively high degree of solubility in alcoholic solvents at temperatures significantly above room temperature as described in Linke, W. F., *Solubilities of Inorganic and Metal Organic Compounds*, Washington, DC, American Chemical Society, Vol. 1 (1958). It has been further noted that solvent conductivity-based detection systems have already been commercially designed to analyze gas chromatographed process streams (see Jones, P., et al, "Versatile Electrolytic Conductivity Detector for Gas Chromatography," *J. Chromatogr.* 73, pp. 19-28 (1972); Hall, R. C. "A Highly Sensitive and Selective Microelectrolytic Conductivity Detector for Gas Chromatography," *Journal of Chromatographic Science*, Vol. 12, pp. 152-160 (1974); Anderson, R. J., et al. "Hall Bipolar Pulse, Differential Electrolytic Conductivity Detector for GC: Design and Applications," *American Laboratory*, pp. 108-124 (1980).

The present invention is based, in part, on an application from the foregoing that an on-line, conductivity-based analytical method could be developed for HCl analysis if a solvent were used which maintained a selectively high HCl solubility at a temperature above the dew point of water in the measurement system (so that sample processing would not include water removal which could potentially remove the analyte). Further, if selective dissolution of HCl is achieved, continuous sampling is possible (since a prior separation step would not be required) and adsorption effects encountered when processing a slug of HCl are reduced because adsorption sites will eventually saturate. The method and apparatus of the invention provide a solution to these and other problems and provide an effective technique for HCl monitoring in connection with a gasification process stream.

In accordance with one aspect of the invention, a method is provided for monitoring the amount of HCl in HCl containing gasification process stream or other HCl process gas streams, said method comprising measuring the initial conductivity of a high boiling point alcohol solvent capable of being protonated by HCl at a high temperature; mixing the solvent with the HCl containing process stream at high temperature to protonate the solvent and thereby increase the conductivity therefrom; measuring the increasing conductivity of the solvent as an indication of the amount of HCl in the process stream.

Preferably, the method includes supplying the HCl containing process stream to a reactor to remove selected constituents therefrom prior to mixing of the process stream with the solvent.

The solvent preferably comprises a cis-and-trans mixture of 1, 3 cyclohexanodiol.

Advantageously, the steps of measuring the initial conductivity of the solvent, mixing of the solvent with the process stream and measuring the increased conductivity of the solvent are performed using a conductivity cell. A mass flow controller is preferably used to control the flow of the process stream to the conductivity cell, and the method advantageously includes the step of separating water vapor and the solvent from the process stream prior to control of the flow by the mass controller. The separating step preferably comprises three stages of separation at different, progressively lower temperatures.

In accordance with a further aspect of the invention an apparatus is provided for monitoring the amount of HCl in a HCl containing gasification process stream or in another HCl containing process gas stream, the apparatus comprising: a reactor, to which the process stream is applied, for removing selected constituents from the process stream to produce an analyte gas stream; means for storing a high boiling point solvent capable of being protonated by HCl at a high temperature; and a conductivity cell, to which the analyte gas stream and the solvent are selectively supplied, for measuring the reference conductivity of the solvent, for mixing the solvent and the analyte gas stream, and for measuring the changed conductivity of the solvent after mixture thereof with said analyte stream to thereby provide an indication of the amount of HCl in the process stream.

Preferably, the apparatus includes means for delivering the solvent to the conductivity cell at a high pressure sufficient to maintain solvent flow to the cell. Advantageously, the means for delivering said solvent comprises a microgear pump.

In a preferred embodiment, the solvent storing means comprises a solvent reservoir comprising a housing containing the solvent such that a vapor pressure exists above the solvent, and the apparatus further comprising an open tube connecting the vapor pressure above the solvent to the gas pressure of the cell.

Preferably, a KOH trap is connected between the cell and the means for storing said solvent for preventing HCl from diffusing into the solvent storing means.

Advantageously, temperature control is provided by a gas chromatographic oven in which the cell and the solvent storing means are housed.

As mentioned above, a gas-solvent separating means, connected to the conductivity cell, is provided for separating said solvent and water vapor from the analyte gas and preferably comprises a plurality of separator stages for providing separation at different, progressively lower temperatures. In an advantageous embodiment, the separating means comprises three separating stages. Preferably, a temperature and pressure regulating means is provided for regulating the temperature and pressure of the process stream applied to the conductivity cell.

Other features and advantages of the invention will be set forth in or apparent from, the description of preferred embodiments of the invention which follows.

DESCRIPTION OF THE PREFERRED EMBODIMENTS

Turning to a consideration of preferred embodiments of the invention, examples of the invention will be described in connection with the analysis of a synthetic gasification stream. Constituents of the synthetic gasification stream used in the examples to be considered are set forth in the following table:

| | | |
|---|---|---|
| 1. benzene | 250 | ppm |
| toluene | 250 | ppm |
| o-xylene | 166 | ppm |
| p-xylene | 166 | ppm |
| m-xylene | 167 | ppm |
| $CO_2$ | 20 | Percent |
| CO | 35 | Percent |
| $H_2$ | 35 | Percent |
| $CH_4$ | 5 | Percent |
| $N_2$ | 5 | Percent |
| 2. $NH_3$ | 1,000 | ppm |
| $N_2$ | Balance | |
| 3. $H_2S$ | 1 | Percent |
| $H_2$ | Balance | |
| 4. $SO_2$ | 1,000 | ppm |
| $N_2$ | Balance | |
| 5. HCN | 500 | ppm |

-continued

| | | |
|---|---|---|
| $N_2$ | Balance | |
| 6. HF | 1,000 | ppm |
| $N_2$ | Balance | |
| 7. HCl | 105 | ppm |
| $N_2$ | Balance | |
| 8. HCl | 505 | ppm |
| $N_2$ | Balance | |
| 9. HCl | 1 | Percent |
| $N_2$ | Balance | |

All of the gas constituents were obtained as mixtures, and the gas cylinders containing these mixtures are represented by the groupings shown in the table. The method used to blend and add water to make the synthetic gas stream involved the use of a manifold or conduit 10 (FIG. 1) to which the constituents were supplied. All gases were preheated to 500° C. before blending to prevent ammonium chloride formation. A multirate infusion (syringe) pump was used to deliver water to the stream. The water was degassed and heated to 99° C. before it was vaporized. Check valves (not shown) were used to prevent back mixing of gases and to isolate the syringe from sudden backpressure increases produced when the water was vaporized. The amount of water introduced into the gas stream per unit time was determined by reading the gradiations on the syringe. Three certified standard HCl cylinders were used to cover a broad concentration range. The gases were accurately blended using a set of calibrated rotometers.

Figure 1:
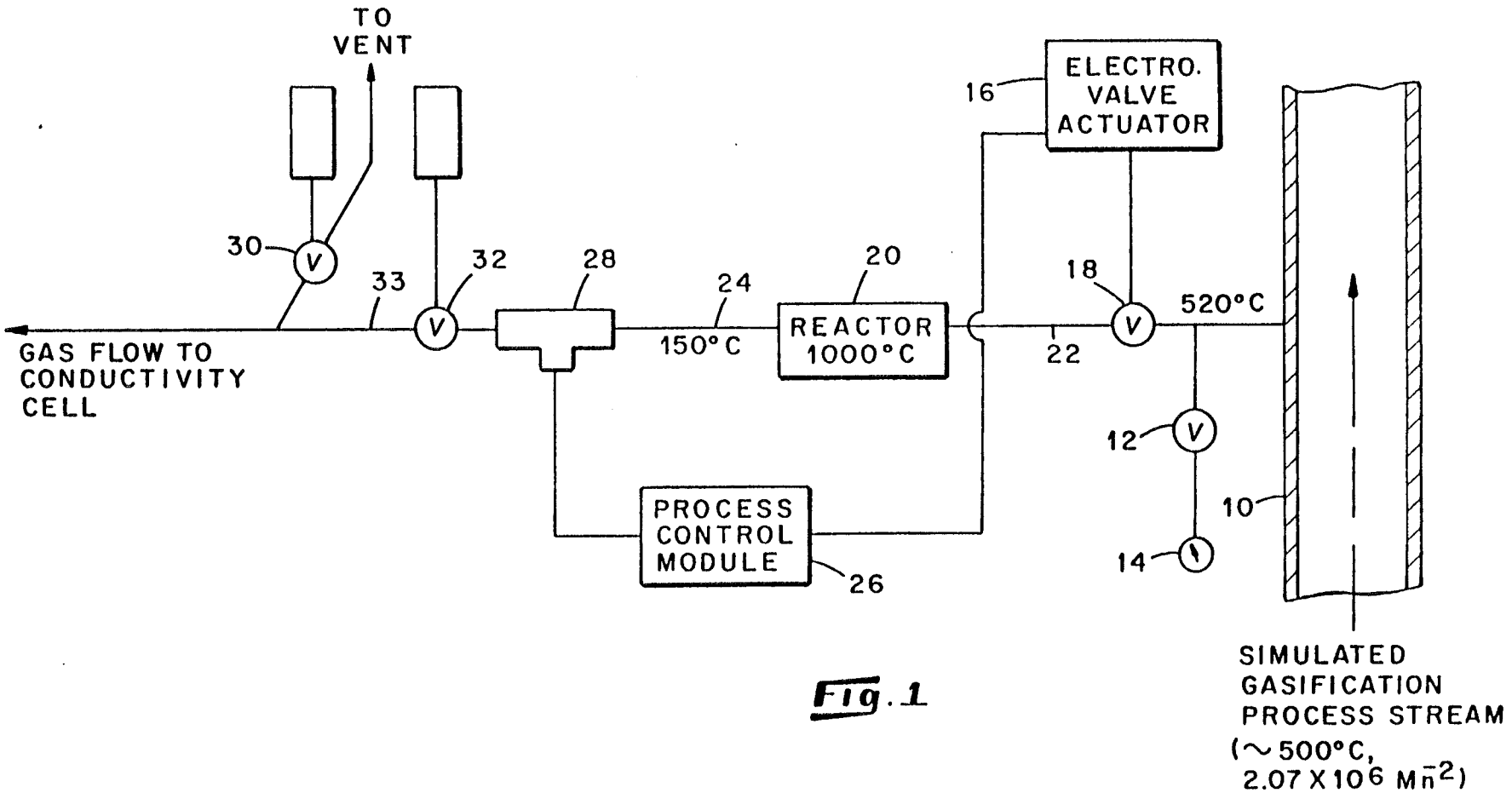
FIG. 1 is a schematic block diagram of a pressure and temperature control system used in introducing a sample stream into the conductivity cell of the system of FIG. 2.

After blending, the gas was heated to 500° C. and pressurized as is indicated in the schematic diagram of FIG. 1 wherein the conduit carrying the simulated gasification process stream is, as noted above, indicated at 10. The pressure of the synthetic gas was calculated assuming ideal behavior using the temperature of the synthetic gas and the room-temperature pressure of the gas measured using an arrangement including a shut-off valve 12 and a gauge 14 upstream of an electromechanical valve actuator 16 which controls a regulating valve 18. The partial pressure of water was assumed to be negligible. The shut-off valve 12 was placed on the gas line leading to the pressure gauge 14 was pressure being measured only periodically so that water condensation and analyte loss were avoided. The pressure of the synthetic gas at the input to the electromechanically operated valve 16 was adjusted by changing the pressure of the gases feeding the rotometers (not shown) referred to above. A typical synthetic gas pressure was 250 psig (calculated).

Figure 2:
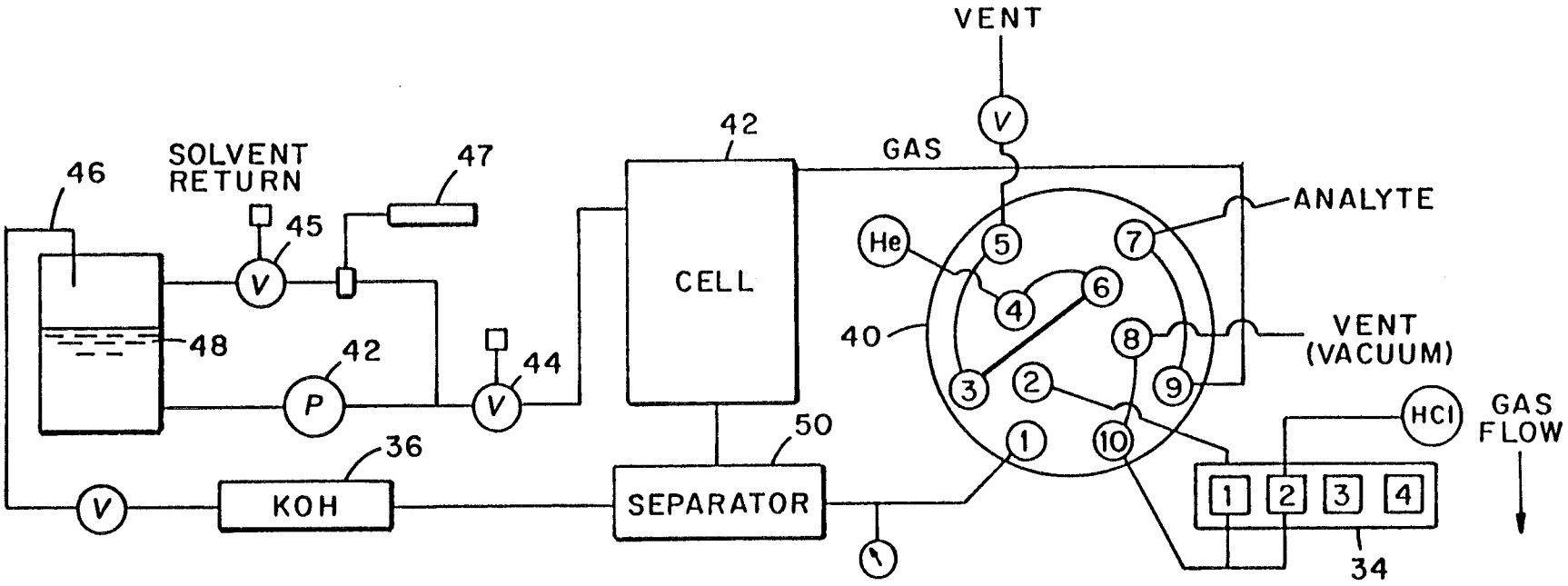
FIG. 2 is a schematic block diagram of the basic components of the HC1 monitor and calibrator unit of the invention, showing the connections of the control valve thereof for the monitoring mode of operation.
Figure 3:
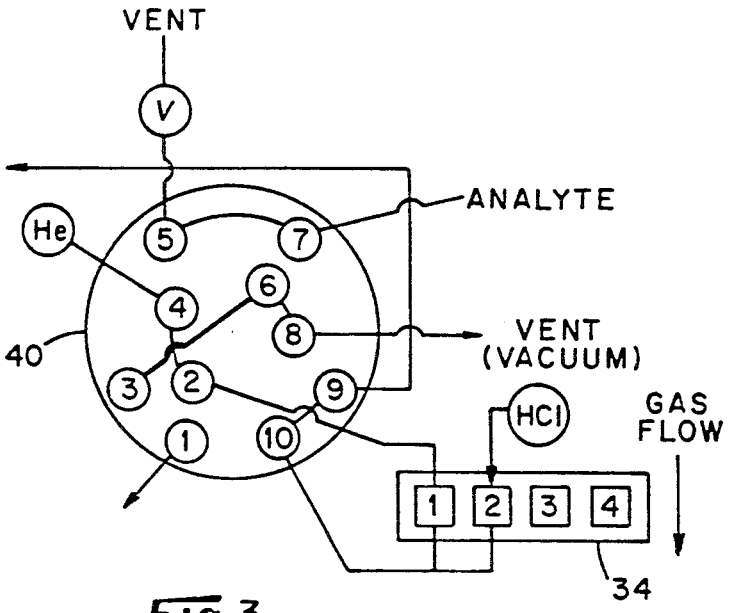
FIG. 3 is a schematic block diagram of the control valve and associated components of FIG. 2, showing the connections of the control valve for the calibration mode of operation.

A complete schematic of the overall HCl monitoring system is shown in FIG. 1 taken with FIGS. 2 and 3. FIG. 1 shows the arrangement used to step shown and control the pressure and temperature of the simulated gasification process stream. This arrangement includes a reactor 20 located downstream of regulating valve 18. In a preferred embodiment, a 20 m by 0.16 cm O.D. by 0.10 cm I.D. coiled length of nickel tubing heated to 1,000° C. was used as the reactor 20 whose purpose was to pyrolyze volatile tars and to catalytically decomposed ammonia. The gas line 22 leading to the reactor was kept slightly above the analyte stream temperature. The gas line 24 downstream of the reactor was heated to 150° C. The reactor operating conditions and dimensions were selected based on an experimental determination of the minimum residence time required for the pyrolysis of benzene at 1,000° C. This was done on the basis that if reactor conditions were severe enough to break aromatic ring, then volatile tar would also pyrolyze. The length of the reactor tube of reactor 20 permitted a gas flow up to 1,500 ml per min before the gas residence time decreased to below the minimum acceptable duration. Decomposition of ammonia to nitrogen and hydrogen was found to occur at a much shorter residence time than benzene.

The pressure regulating system was designed to operate at a maximum temperature and pressure of 600° C. and $2.07\times10^{6}$rm$^{-2}$. In a specific example, the regulating valve 18 was an SS-4URW-HT high-temperature bellows valve (NUPRO) with the valve stem mechanically connected to the electromechanical valve actuator 16 (HOKE). The valve actuator 16 was controlled using a process control module 26, preferably a CN2002V5 programmable process controller (OMEGA) operated with dual proportioning, integral, derivative control. Thus, the voltage supplied to the induction coils of actuator 16 decreased as the pressure set point was approached from above or below. This arrangement kept oscillations about the set point to $\pm3.4\times10^{4}$nm$^{-2}$. In between the regulating valve 18 and a metering valve 32, pressure was maintained at the set point with this pressure being used to drive the sample through the HCl monitoring conductivity cell (See FIG. 2). Using this control system, it was determined that very rapid pressure changes (as large as $3.5\times10^{5}$nm$^{-2}$), such as could occur in a real or actual gasification stream, did not affect the gas flow through the conductivity cell.

A pressure transducer 28 is connected to reactor 20 downstream thereof. In a preferred embodiment, a PX 951-200G 5V pressure transducer (OMEGA) was used to monitor the preset pressure and to provide input to the controller 26. A vent valve 30 was required because without this vent the gas demand of the monitor was too small to prevent the regulating valve 18 from fully seating, a condition that facilitated pressure set point overshoot and undershot. The vent valve 30, the metering valve 32 connected downstream of transducer 28 and the transducer 28 itself were all heated to 150° C.

Referring to FIG. 3, the critical components of the monitoring and calibration system are shown. Except for mass flow controller 34, a KOH trap 36, and the pressure radouts referred to below, and the second and final gas/solvent separator stages shown in FIG. 4, all components were housed in a gas chromatographic oven at 125° C. An air actuated 10-port control valve 40 (VICI) provided rapid switching between calibration and analysis modes of operation, with the calibration mode being shown in FIG. 3. In the analysis mode shown in FIG. 2, the analyte stream (from FIG. 1) was routed through the 10-port valve 40 into a conductivity cell 42. The conductivity cell 42 is preferably a Hall differential electrolytic conductivity cell (TRACOR). The measurement of the solvent (reference) conductivity, the mixing of the solvent with the analyte gas stream, and the measurement of the changed conductivity of the solvent are all internal functions of the cell 42, with this operation being fully described in "Operations Manual for 700A Electrolytic Conductivity Detector," Tracotr Instruments, Analytical Division (1982). In this exemplary embodiment, the TRACOR standard 700A signal processing module was used for cell excitation and signal amplification. The amplified output of cell 42 was monitored on an HP 3390A (Hewlett-Packard) reporting integrator (not shown). In the exemplary embodiment, the conductivity cell 42 was modified for high-temperature operation by replacing the Kel-F gas liquid contractor with a TFE Teflon gas liquid contactor. It was determined that when exposed to hot alcoholic solvents, the Kel-F material developed spherulitic domains that significantly restricted gas and solvent flow.

The solvent used in the exemplary embodiment under consideration was a cis-and-trans mixture of reagent grade 1,3-cyclohexanediol (FLUKA). The solvent was delivered to the conductvity cell 42 at high pressure (typically $8.3\times10^{5}$ nm$^{-2}$) using a microgrear pump 44 with a restrictor or metering valve 46 disposed in between the pump 44 and the conductivity cell 42. A further metering valve 45 and pressure indicator assembly 47 were connected in the solvent return line, as illustrated. In a specific example, the pump head was housed in the oven and the pump motor protruded out of the oven and was cooled by room temperature. The response of the cell 42 to HCl was found to be very solvent flow dependent and it was necessary to deliver the solvent to the cell at high pressure to help maintain constant solvent flow despite the unavoidable gas pressure fluctuations inside the cell 42.

To further enhance solvent flow stability, an open tube 46 was used to connected the vapor pressure above a solvent reservoir 48 with the gas pressure of the cell 42 as shown in FIG. 2. Thus, there was never a pressure differential across the pump 42 that was not produced by the pump itself. The KOH trap 36, which was referred to above, was incorporated in the line connected to tube 46, had no restriction and was used to prevent any HCl from diffusing into the solvent reservoir 48. Pressure fluctuations within the cell 42 were caused by the re-mixing of solvent and gas just before exiting the cell 42 (another internal function of the cell). Enough solvent would periodically collect in the line leading to a first-stage separator, indicated at 50, to cause a momentary blockage which was pushed into the separator 50 after sufficient buildup of gas pressure. The open tube 46 was placed as close to the exit port of cell 42 as possible so that the position of tube 46 was above the point where solvent blockage occurred.

As illustrated in FIG. 2, gas flow through the conductivity cell 42 was controlled after exiting the cell 42 in the analysis mode of operation and, as illustrated in FIG. 3, was typically controlled before the cell 42 in the calibration mode of operation. This scheme was necessary since water present in the analyte stream cannot be removed without loss of solute (HCl), and the mass flow controller 34, which was referred to above, cannot be operated above the boiling point of water. The controller 34 used in the example being considered was an FM4585 multiple channel mass flowmeter and flow controller (Linde) equipped with 11C and 6C flow control modules in Channels 1 and 2, respectively. Channel 1 was factory calibrated on gas mixture No. 1 of the table above and delivered a stable gas flow (fluctuation less than 1 mL per min) with an accuracy of $\pm3$ percent of the present flow rate over an inlet pressure range of 0 to $1.0\times10^{7}$nm$^{-2}$. Channel 2 was factory calibrated on gas mixture No. 7 of the table above and delivered a stable gas flow with an accuracy of less than $\pm5$ percent of the readout value. A pressure drop of at least $1.4\times10^{5}$ nm$^{-2}$ across the flow control module 34 was required to maintain stable gas flow at the flow rate used for analysis. The nominal maximum pressure that the conductivity cell 42 could withstand without leakage was about $1.4 \times 10^5 nm^{-2}$ (gauge), and so a vacuum was applied to the effluent side of the flow controller 34 so that the cell 42 did not have to be operated at its maximum pressure tolerance level. When the operative mode of the HCl monitor was switched from analysis to calibration as indicated by comparing FIG. 3 with FIG. 2, the three-way valve of FIG. 3 was turned to route the calibration gas stream through a restrictor (not shown) so that system pressure was maintained. Likewise, the rerouted analyte stream was passed through a restrictor (not shown) that had been matched to the gas demand of the monitor so that the pressure step-down and control system was not interrupted.

Figure 4:
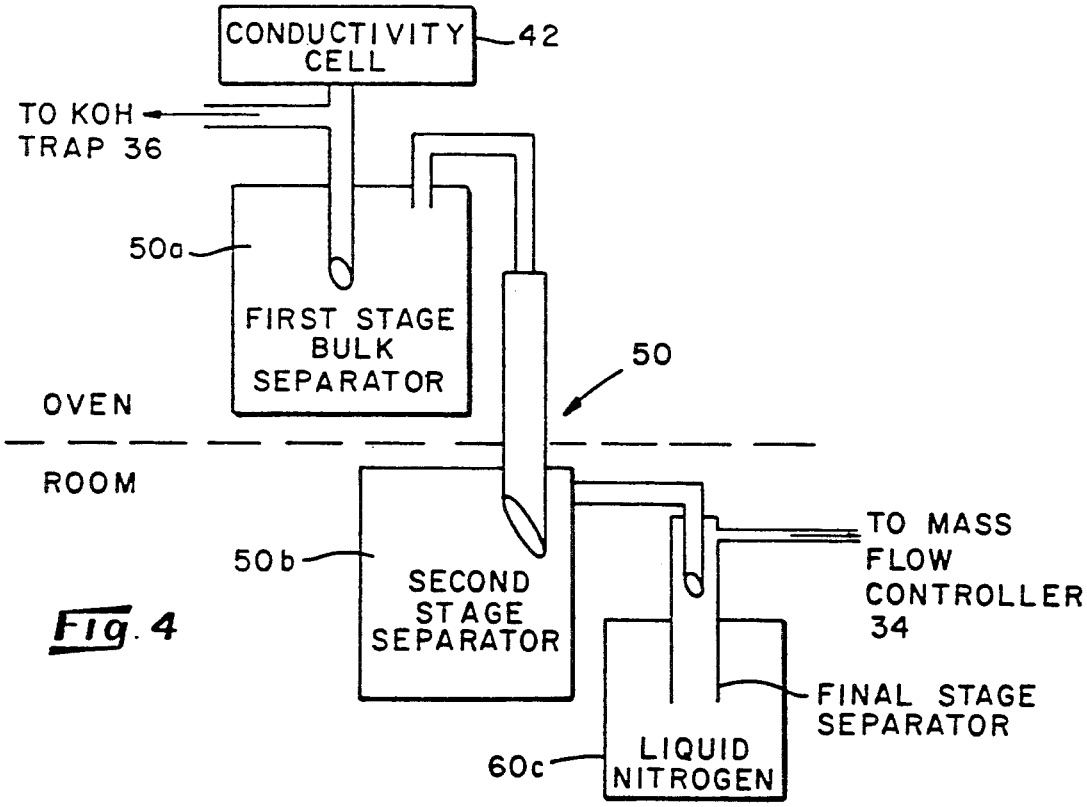
FIG. 4 is a schematic diagram of the gas-solvent separation stages employed with the monitor of FIG. 2.

As illustrated in FIG. 4, in order to ensure stable gas flow it was necessary to separate the solvent and water vapor from the analyte gas prior to the mass flow controller input and control. As illustrated in FIG. 4, several stages of separation were used, starting with a bulk separation, indicated 50*a* in FIG. 4, inside the oven with the remaining stages 50*b*, 50*c* being performed outside the oven. The second stage 50*b* is used to separate solvent and water vapors that condensed at room temperature from the gas. The final stage 50*c* used a liquid nitrogen chilled cold finger to dry the gas prior to input into the mass flow controller. Therefore, HCl measurements were reported on a dry basis.

Considering the results produced by the system of FIGS. 1 and 2, a one-to-one linear relationship between detector response with both gas and solvent volumetric flow rates was observed within the HCl solubility limits of the solvent. Response was inversely proportional to solvent flow and directly proportional to gas flow. The relationship indicated that the time required for establishment of steady-state equilibrium of HCl between the gas phase and the liquid phase was much faster than the average gas/liquid contact time. Thus, increasing gas flow or decreasing solvent flow produced a preconcentration of analyte in the solvent prior to the conductivity measurement.

Figure 5:
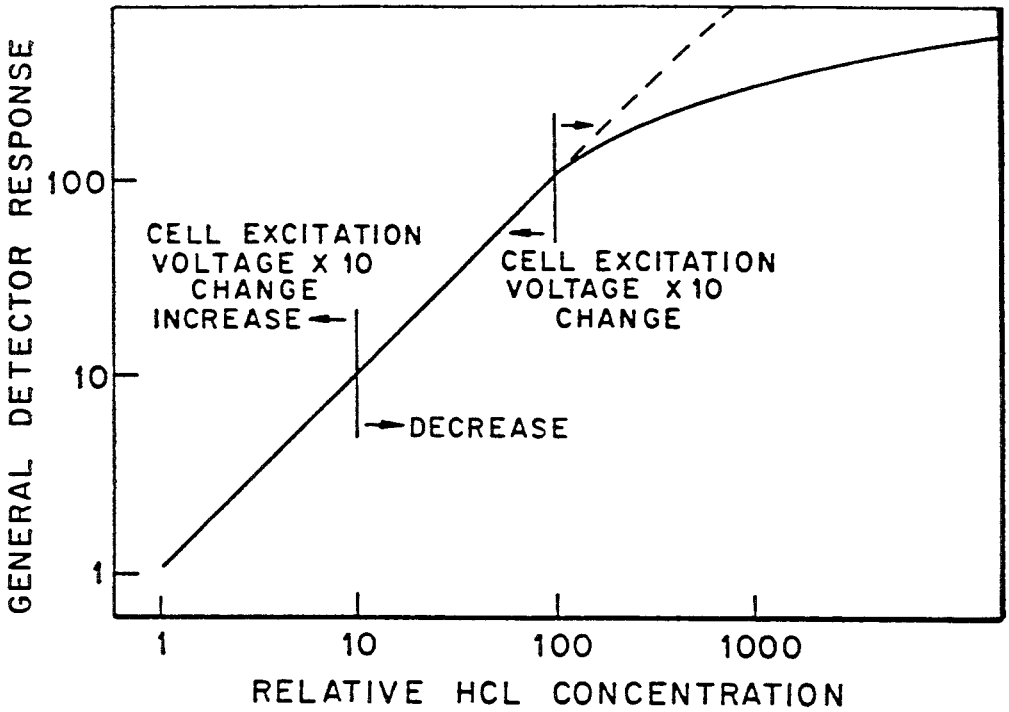
FIG. 5 is a graphical representation of the general response of the detector (monitor) as a function of HCl concentration.

In a plot of detector response versus HCl concentration shown in FIG. 5, the response leveled off after about 2 decades of concentration increase due to solvent saturation. The bottom end of the curve was defined by the lower detection limit for a given set of operating conditions. The lower limit of detection was chosen as three times base line noise which was typically 0.3 percent of full scale. The actual concentrations to which the calibration curve is applicable depends on the value of the gas flow to solvent flow rate ratio selected. In general, a high ratio was selected for low concentrations so that the HCl was sufficiently preconcentrated in the solvent and a large enough response was produced. For a stream having a high HCl concentration, a low ratio was selected to avoid saturation.

As indicated in FIG. 5, the excitation of cell 42 was varied by 1 decade to cover the linear portion of the calibration curve. The cell excitation module referred to above provided selection of cell excitation voltage ranging in decade steps from ±0.007 to +7 volts. However, due to excessive base line noise at large excitation voltages, the HCl monitor was always operated between +0.007 and +0.7 volts. To achieve adequate sensitivity at low HCl concentration the solvent flow was reduced or the gas flow was increased or both. Care must be exercised to ensure that the concentration range of the analogy stream was within the linear portion of the calibration curve. In practice, the gas-to-solvent flow ratio was set to produce a linear response based on a prior knowledge of the composition of the analogy stream. The ratio was adjusted so that the average concentration of HCl in the analyte stream fell in the middle of the calibration curve. The limitations of the HCl monitor resulting from this adjustment requirement and the 2-decade dynamic linear range are discussed below.

Figure 6:
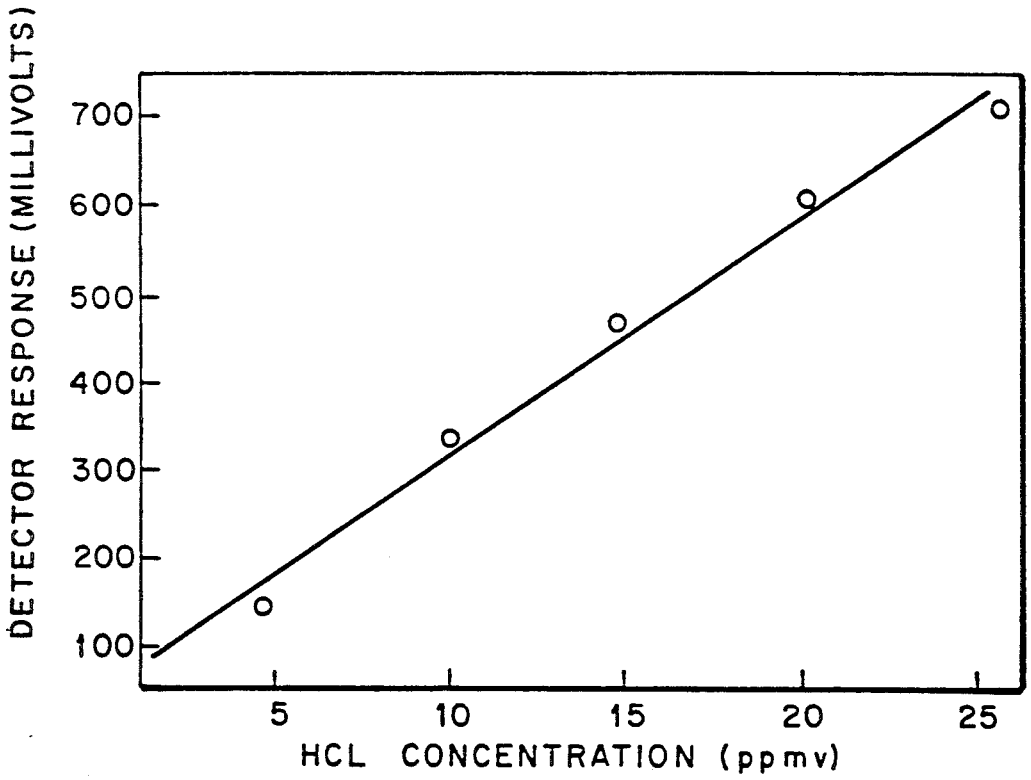
FIG. 6 is a typical response curve of the detector (monitor) as a function of HCl concentration generated in the monitoring (analysis) mode of operation under experimental conditions discussed below.

A typical response curve is shown in FIG. 6, wherein the curve shown was generated in the analysis mode of operation under experimental conditions listed in the table which follows. For each specific point plotted FIG. 6, the HCl concentration was held constant while the concentrations of $H_2O$, $NH_3$, $H_2S$, $SO_2$, HCN, and HF were varied. The balance gases for the latter five gases listed above affected the concentration of the first 10 gases shown in the table (and thus, the concentration ranges). Each HCl concentration data point is an average of seven determinations. The first determinations was made in a sample matrix comprised of HCl and the first 10 gases of the table. The six remaining determinations were made by first adding 100 ppmv $NH_3$ followed by 1,000 ppmv $H_2S$, etc. The average relative standard deviation for each data point of FIG. 6 was 3 percent.

| GAS STREAM COMPOSITION | | OTHER CONDITIONS | |
|---|---|---|---|
| $N_2$ | 5 to 36 percent | Synthetic Gas Temperature[2] | 525° C. |
| $H_2$ | 24 to 35 percent | Synthetic Gas Pressure[2] | $1.4 \times 10^6$ $nm^{-2}$ (Gauge) |
| CO | 24 to 35 percent | Reactor Temperature | 1,000° C. |
| $CO_2$ | 14 to 20 percent | Analysis Temperature | 130° C. |
| $CH_4$ | 3 to 5 percent | Cell Gas Pressure | $8.3 \times 10^4$ $nm^{-2}$ (Gauge) |
| Benzene | 171 to 248 ppmv | Solvent Pressure | $6.9 \times 10^5$ $nm^{-2}$ (Gauge) |
| Toluene | 171 to 248 ppmv | Solvent Flow Rate | 0.5 mL/min |
| o-xylene | 114 to 164 ppmv | Gas Flow Rate Through the Cell | 260 mL/min |
| p-xylene | 114 to 164 ppmv | | |
| m-xylene | 115 to 165 ppmv | | |
| $NH_3$ | 0 to 100 ppmv | | |
| $H_2S$ | 0 to 1,000 ppmv | | |
| $SO_2$ | 0 to 10 ppmv | | |
| HCN | 0 to 5 ppmv | | |
| HF | 0 to 10 ppmv | | |
| $H_2O$ | 0 to 20 molar percent | | |
| HCL | 5 to 24 ppmv | | |

[1]Dry basis
[2]At the inlet to the electromechanically operated regulating valve.

The response of the monitor was absolutely HCl-specific when monitoring the synthetic gasification process stream. All known and suspected gasification process stream constituents (as well as some combustion stream constituents) list above were tested for detector response, both individually and as mixture. Some components were tested for response at concentrations far in excess of their typical or suspected concentrations. No measurable matrix effects were observed when the cell excitation voltage was kept below +0.7 volts. At extreme sensitivity (i.e., 7 volts cell excitation voltage), a slight response to $SO_2$ was observed. For these examples, $SO_2$ in a balance of nitrogen was run with the analyzing system operating in the calibration mode. The vent restriction shown in FIG. 2 was removed so that gas flows in excess of 1,000 mL per min could be obtained to maximize preconcentration. The solvent flow rate was also adjusted to maximum. Thus, the response curves that were produced are of the maximum possible response and the low maximum response to $SO_2$ that as noted indicates that the maximum steady-state concentration of dissolved $SO_2$ is neglible under normal gasified conditions. Similar experiments were done with HF and $H_2S$ at maximum concentrations of 1,000 and 10,000 ppm, respectively. Responses to these species were at least over an order of magnitude less than the maximum $SO_2$ response. It was not determined why $SO_2$ produced a larger response when compared to $H_2S$ and HF. When water vapor was introduced into the gas stream along with $SO_2$ no increase in response was observed. Since the $SO_2$ response was low in this circumstance, it was clearly not acting as a Bronsted acid in the 1,3-cyclohexanediol solvent. When HBr was tested, the response was comparable to the HCl response. The HBr test confirmed the basis of selectively of the detection system.

Tests were also performed to evaluate the affects of changing cell gas pressure on the HCl response. Cell gas pressures were varied from $3.5\times10^4$ to $1.4\times10^5$ $nm^{-2}$ (gauge) at a constant gas flow/HCl concentration. The gas to solvent flow rate was adjusted so that the influent HCl concentration generated a response corresponding to the middle linear range of the calibration curve. Under these conditions, cell pressure had no effect on response which indicated that HCl dissolved into the solvent quickly and that HCl partial pressure beyond the gas-liquid contacting region of the conductivity cell 42 was negligible.

Although the linear dynamic range of the HCl monitor was two orders of magnitude, its operating range covered six orders of magnitude. Solvent flow was variable from 0.05 to 5 mL/min. Solvent flow greater than 5 mL/min caused blockage of the KOH tube 35 of FIG. 2 which in turn increased detector baseline fluctuation. At solvent flows less than 0.05 mL/min, evaporative solvent loss prevented adequate wetting of the conductivity cell electrodes. In addition, at very low solvent/gas flow ratios, inadequate mixing of solvent and gas occurred. Gas flow in the analysis mode was variable from 50 to 400 mL/min. At gas flow less than 50 mL/min, KOH tube blockage occurred. Gas flow greater than 500 mL/min could not be obtained without exceeding the safe maximum operating pressure. Combining the operational solvent and gas flow ranges with the three decade span of the excitation voltage of cell 42, an operating range of $10^6$ has been achieved. By proper adjustment of the cell excitation voltage, gas flow, and solvent flow, it was experiemental determined that analyte streams ranging in HCl concentrations from 100 ppb to 10 percent V/V could be analyzed.

It was observed in these experiments that there was a lag time between introduction of HCl and when the first response was observed, and this is a consequence of the absorptive nature of HCl. The leading front of the HCl may take up to several hours to reach the detector when the system is first used or when the system has been purged with helium for several days. After initial breakthrough, the response per known HCl concentration was seen to gradually rise to a constant value. At that point adsorption sites were covered and the system response time to concentration changes was approximately equivalent to the length of tubing that HCl traveled through divided by the linear gas flow velocity. The total length of tubing in the described laboratory version of the HCl monitor was about 2,700 cm. Thus, the response time ranged from 1.7 minutes to 10 seconds over a gas flow range of 50 to 500 mL/min.

Because of the relatively narrow linear dynamic range, the HCl monitoring method of the invention may not be well suited for monitoring process streams in which large and rapid HCl concentration changes occur. A possible additional problem that also arises when rapid and large concentration changes occur in the analyte stream is related to the absorptivity of HCl on exposed surfaces. Partitioning of HCl between the gas phase and the gas-solid interface of the inner walls of the tubing seems to be concentration dependent. This phenomenon leads to the generation of a "memory" effect which reflects the time required for the adsorbed HCl on the surfaces to establish an equilibrium with the HCl in the analyte gas stream. This effect could be significant if the amount of "excess" HCl desorbed into the gas phase is comparable to analyte HCl concentration. The amount of time for equilibration to reestablish was shown to be dependent on both the magnitude of analyte concentration change and the magnitude of the "new" analyte concentration. This effect is clearly observed in tests wherein HCl concentrations were reduced by one-half in successive steps. In these tests the time required to reach a new equilibrium becomes longer at lower HCl concentrations. Similar memory effects were observed for concentration increases.

The described HCl monitoring method is applicable for the analysis of certain types of process streams. With the reactor in operation, the monitor could not be used to accurately monitor HCL in process streams containing chlorinated organics. However, the monitor could be used to measure gross levels of chlorinated organics in process streams not initially containing HCl. The monitor could be used on process streams containing chlorinated organics if significant amounts of condensables and ammonia were not present in the stream and one could bypass the pyrolysis reactor. In addition, the monitor will detect all very strong Bronsted type acids such as HBr, $HNO_3$, and $H_2SO_4$. In as much as bromine is a low ppmv coal constituent (compared to chlorine which is a low ppmv coal constituent) and nitric and sulfuric acids are not gasification products, only HCl is detected in the application of the method of the invention to the analysis of gasification process stream. The monitor may be useful for monitoring coal combustion streams, even though all the precursors of sulfuric and nitric acids may be present in these streams, in that the rate of formation of these acids is exceptionally slow and should not interfere with HCl analyses.

Although the present invention has been described relative to specific exemplary embodiments thereof, it will be understood by those skilled in the art that variations and modifications can be effected in these exemplary embodiments without departing from the scope and spirit of the invention.

What is claimed is:

1. A method for monitoring the amount of HCl in a HCl containing gasification process stream or in other HCL containing process gas streams, said method comprising:

measuring the initial conductivity of a high boiling point alcohol solvent capable of being protonated by HCl at a high temperature;

mixing the solvent with the HCl containing process stream at high temperature to protonate the solvent and thereby increase the conductivity therefrom; and measuring the increased conductivity of the solvent as an indication of the amount of HCl in the process stream.

2. A method as claimed in claim 1 wherein said solvent comprises a cis-and-trans mixture of 1,3 cyclohexanodiol.

3. A method as claimed in claim 1 wherein the steps of measuring the initial conductivity of the solvent, mixing of the solvent with the process stream and measuring the increased conductivity of the solvent are performed using a conductivity cell.

4. A method as claimed in claim 3 further comprising using a mass flow controller to control the flow of the process stream to the conductivity cell, said method including the steps of separating water vapor and the solvent from the process stream prior to control of the flow by said mass controller.

* * * * *